(12) United States Patent
Picha

(10) Patent No.: US 6,364,858 B1
(45) Date of Patent: Apr. 2, 2002

(54) COLLAPSIBLE INTERNAL BOLSTER FOR GASTROSTOMY DEVICE

(75) Inventor: George J. Picha, Independence, OH (US)

(73) Assignee: Applied Medical Research, Inc., Garfield Heights, OH (US)

( * ) Notice: Subject to any disclaimer, the term of this patent is extended or adjusted under 35 U.S.C. 154(b) by 0 days.

(21) Appl. No.: 09/052,167

(22) Filed: Mar. 31, 1998

(51) Int. Cl.[7] .............................................. A61M 29/00
(52) U.S. Cl. ........................ 604/174; 604/910; 604/174
(58) Field of Search ................................ 604/174–175, 604/264, 93, 275, 277–278, 523, 528, 910, 96.01, 104–108, 270, 514, 516, 93.01, 77, 79, 80

(56) References Cited

U.S. PATENT DOCUMENTS

| | | |
|---|---|---|
| 3,575,160 A * | 4/1971 | Vass |
| 3,951,153 A | 4/1976 | Leucci |
| 4,059,111 A | 11/1977 | Erasmus |
| 4,311,148 A | 1/1982 | Courtney et al. |
| 4,315,509 A | 2/1982 | Smit |
| 4,516,578 A | 5/1985 | Shuffield |
| 4,573,576 A | 3/1986 | Krol |
| 4,629,459 A | 12/1986 | Ionescu et al. |
| 4,668,225 A | 5/1987 | Russo et al. |
| 4,701,163 A | 10/1987 | Parks |
| 4,732,152 A | 3/1988 | Wallsten et al. |
| 4,758,219 A | 7/1988 | Sacks et al. |
| 4,762,519 A | 8/1988 | Frimberger |
| 4,798,592 A | 1/1989 | Parks |
| 4,826,481 A | 5/1989 | Sacks et al. |
| 4,863,438 A | 9/1989 | Gauderer et al. |
| 4,878,906 A | 11/1989 | Lindemann et al. |
| 4,913,141 A | 4/1990 | Hillstead |
| 4,922,905 A | 5/1990 | Strecker |
| 5,007,900 A | 4/1991 | Picha et al. |
| 5,073,166 A | 12/1991 | Parks et al. |
| 5,074,846 A | 12/1991 | Clegg et al. |
| 5,080,650 A | 1/1992 | Hirsch et al. |
| 5,084,014 A | 1/1992 | Picha et al. |
| 5,100,384 A | 3/1992 | McBrien et al. |
| 5,112,310 A | 5/1992 | Grobe |
| 5,147,400 A | 9/1992 | Kaplan et al. |
| 5,167,627 A | 12/1992 | Clegg et al. |
| 5,234,454 A | 8/1993 | Bangs |
| 5,234,456 A | 8/1993 | Silvestrini |
| 5,267,969 A | 12/1993 | Hirsch et al. |
| 5,273,529 A | 12/1993 | Idowu |
| 5,391,159 A | 2/1995 | Hirsch et al. |
| 5,405,378 A | 4/1995 | Strecker |
| 5,417,657 A * | 5/1995 | Hauer |
| 5,476,505 A | 12/1995 | Limon |
| 5,545,141 A | 8/1996 | Eld |
| 5,555,898 A | 9/1996 | Suzuki et al. |
| 5,628,753 A | 5/1997 | Cracauer et al. |
| 5,807,314 A | 9/1998 | Ross et al. |
| 5,910,128 A * | 6/1999 | Quinn |
| 5,941,855 A * | 8/1999 | Picha et al. .................. 604/174 |

* cited by examiner

Primary Examiner—Richard K. Seidel
Assistant Examiner—LoAn H. Thanh
(74) Attorney, Agent, or Firm—Pearne & Gordon LLP

(57) ABSTRACT

A gastrostomy device including a tubular portion having an outer end and an inner end, and an internal bolster integrally attached to the tubular portion inner end and resiliently movable between an installation configuration and a deployed configuration. The internal bolster has an inner surface and an outer surface. The inner surface surrounds the tubular portion inner end and is generally convex in shape. The outer surface includes a planar portion and a concave portion that extends from the planar portion. The bolster is placed in an installation configuration by the cooperative action of a rod member and a suture member. The rod member is inserted into a pocket provided on the outer surface of the bolster, and the suture member is wrapped around internal bolster to keep the internal bolster generally aligned with the tubular portion axis. Removal of the rod member and suture member from the internal bolster permits the internal bolster to return to a deployed configuration generally transverse to the tubular portion axis.

11 Claims, 6 Drawing Sheets

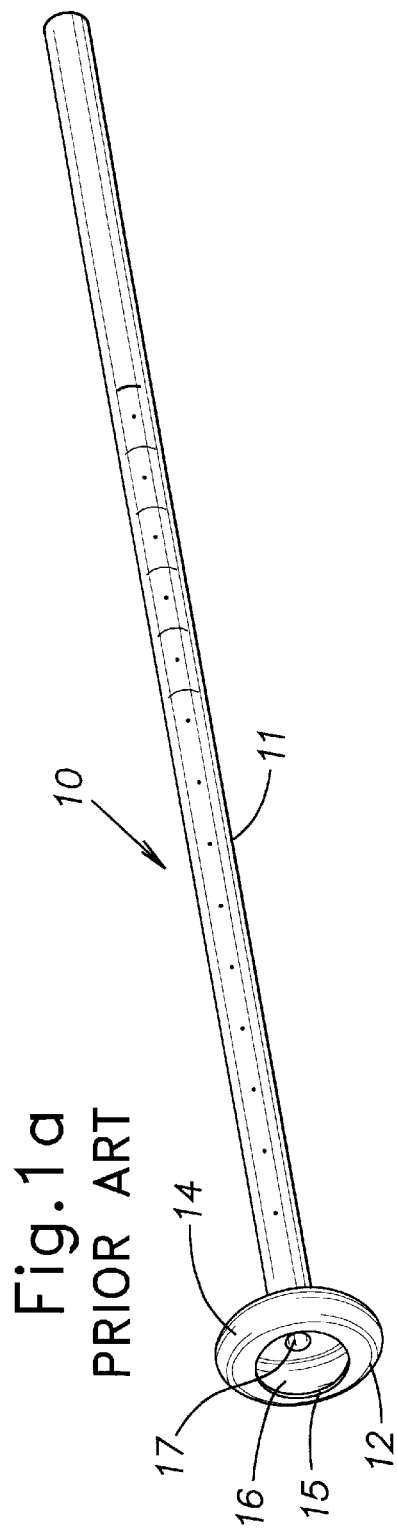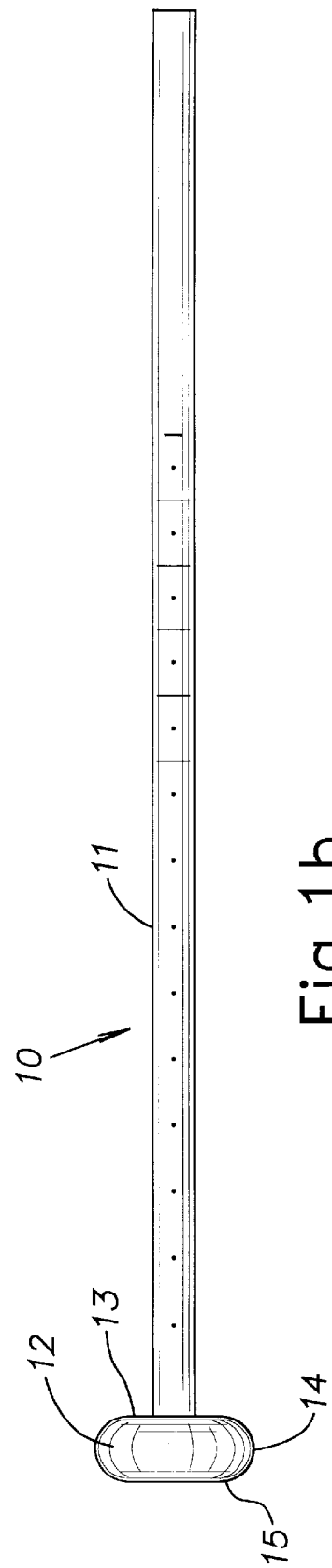

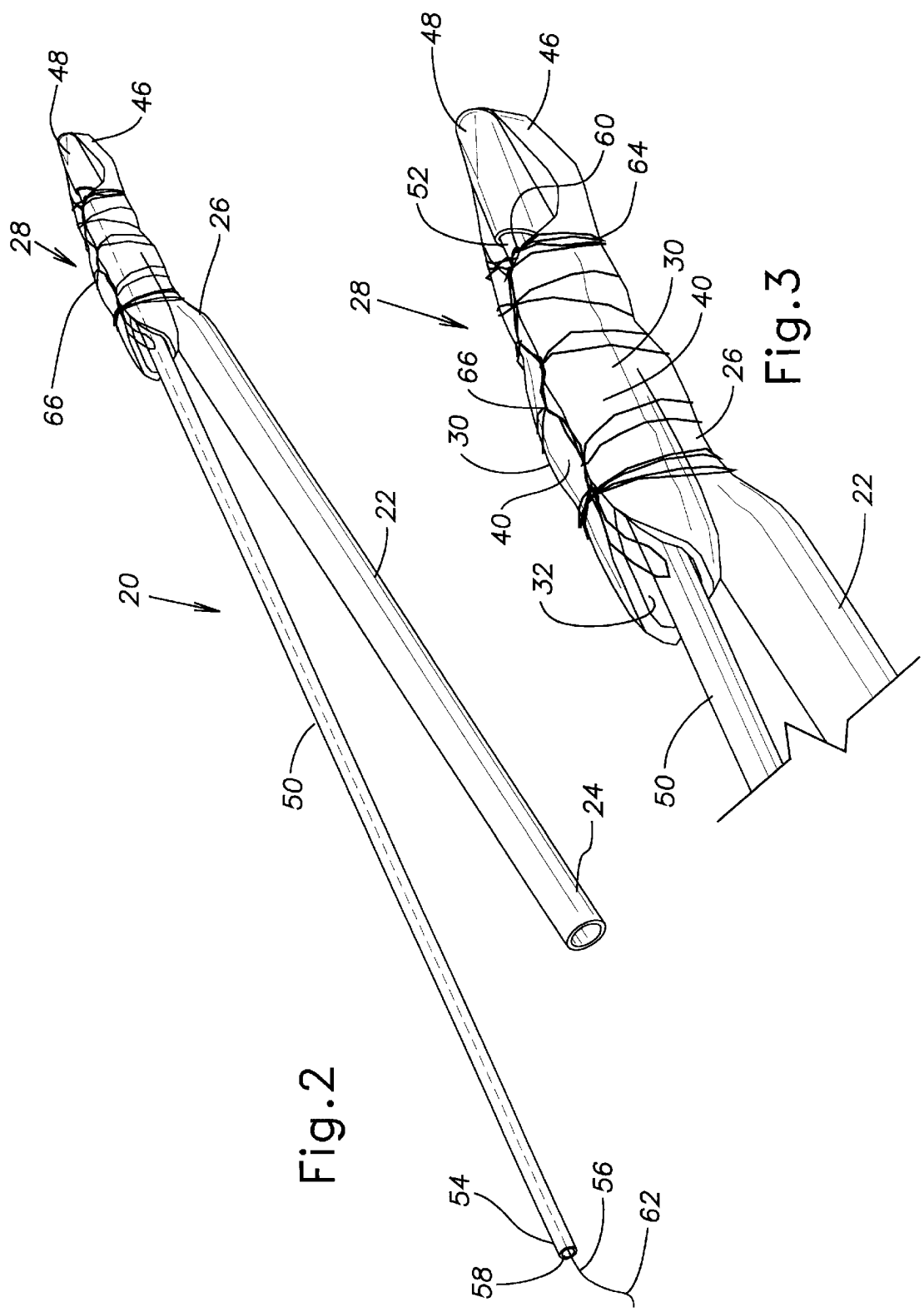

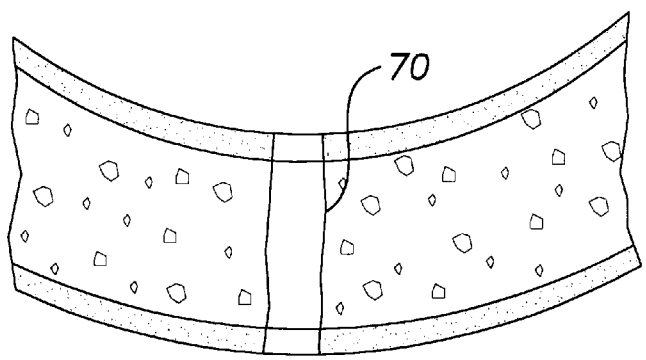
Fig.11
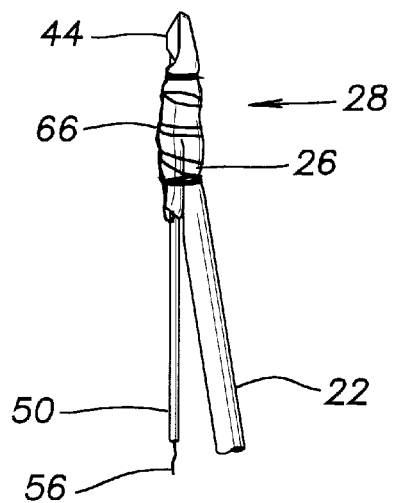
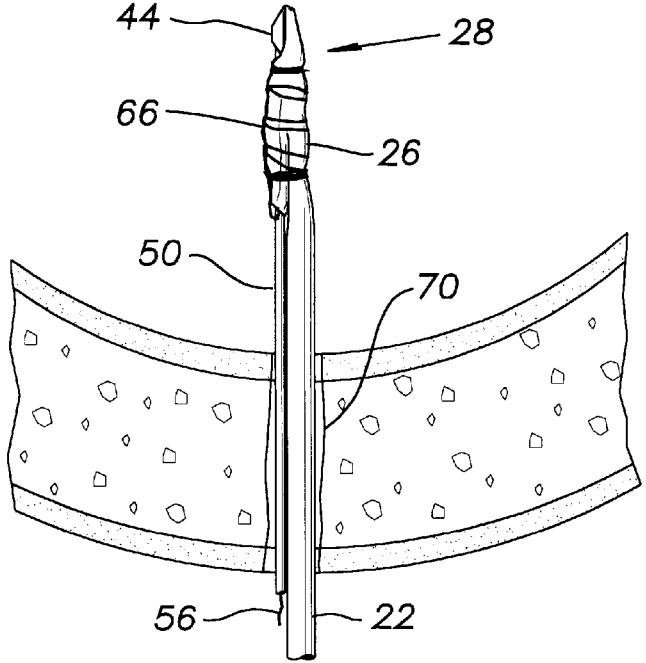
Fig.12

COLLAPSIBLE INTERNAL BOLSTER FOR GASTROSTOMY DEVICE

BACKGROUND OF THE INVENTION

The present invention is generally directed toward a gastrostomy device and, more particularly, toward an internal bolster for such a gastrostomy device.

Several different gastrostomy designs have been developed and employed over the years. Each of these designs has met with varying degrees of success. One of the main reasons for this varying success is the competing and sometimes conflicting design and functional requirements of gastrostomy devices. Firstly, gastrostomy devices should be easy to install within a patient, both for an initial installation and subsequent replacements. Secondly, the gastrostomy device should have an internal bolster which will resist withdrawal forces to prevent inadvertent partial or complete removal of the internal bolster from the patient via the stoma tract. These design considerations tend to conflict with each other since gastrostomy devices which are easily installed have heretofore had undesirably low resistance to withdrawal forces, and gastrostomy devices which provide suitable resistance to withdrawal forces have been difficult or expensive to install and/or replace.

One popular known gastrostomy device, sometimes referred to as a dome-PEG device, is illustrated in FIGS. 1a–1b. The dome-PEG device 10 has a tubular portion 11 with an integral internal bolster 12. The internal bolster 12 has a flat, annular wall 13 radially surrounding an opening 17 of the tubular portion 11 and a curved ring-shaped wall 14 that extends away from the periphery of the annular wall 13 in a direction opposite to the tubular portion. A distal end 15 of the internal bolster defined by the ring-shaped wall 14 provides a circular opening 16 through which material from the tubular portion opening 17 may flow.

An initial or first dome-PEG device 10 is installed in a patient via the esophagus and stomach. The tubular portion 11 is pulled through an incised tract until the annular wall 13 of the internal bolster abuts the stomach lining surrounding the incised tract. As such, the tubular portion extends from the patient's body and may frictionally receive an external bolster to retain the dome-PEG device in place.

An installed dome-PEG 10 is removed from the patient either via the esophagus or by pulling on the tubular portion to overcome the internal bolster's resistance to withdrawal and thereby deforming and pulling the internal bolster through the stoma tract. A subsequent or replacement dome-PEG device is installed identically to the initial or prior dome-PEG device, i.e., via the esophagus.

Accordingly, dome-PEG devices offer the advantage of the satisfactorily high resistance to withdrawal forces while suffering from the disadvantage of requiring installation via the esophagus, which is rather time-consuming for the physician and uncomfortable for the patient.

An alternative to the dome-PEG is commonly known as a stick-PEG, and is exemplified by U.S. Pat. No. 5,007,900, the disclosure of which is expressly incorporated herein in its entirety. The '900 patent device includes a resilient tube having a distal end with a transversely directed internal bolster. The internal bolster has a pocket radially spaced from the tube and adapted to receive a rod. The rod permits proper orientation of the internal bolster and, more specifically, urges the bolster to a stretched position collateral with the tube to facilitate installation of the stick-PEG device within a patient.

Stick-PEG devices are generally installed in existing stoma tracts and are used as replacements for dome-PEG devices due to the former's relatively easy method of installation. However, stick-PEG devices suffer from the disadvantage that, in the minds of some clinicians, the internal bolster surface area may be insufficient to prevent flow of stomach contents around or under the internal bolster. Therefore, there is concern about leakage around the internal bolster and migration of fluid up the tube-tissue interface. Also, medical personnel responsible for installation have indicated some dislike for the manipulation required to install stick-PEG devices within a patient. These disadvantages have limited the acceptance of stick-PEG devices as an alternative to dome-PEGS.

Various other types of PEG devices, and internal bolsters, are known in the art. For example, U.S. Pat. Nos. 4,311,148 and 4,668,225 show feeding tubes or catheters having resilient wing-like protrusions about the end of the tube for retaining the tube within a passage through the wall of a body cavity. The tube is designed to be inserted into the patient through a fresh incision that is then sutured about the tube. To remove the tube from the patient, it is possible to pull the tube through the passage by exerting sufficient force to fold the wings back out of the way.

U.S. Pat. No. 4,573,576, the disclosure of which is expressly incorporated herein in its entirety, shows a catheter with a disk-like retainer on one end. A line is introduced through an incision in the patient's skin, fascia and stomach wall, and an endoscope is used to capture the loose end within the stomach and to draw it out the patient's mouth. The line is then used to draw the tube portion of the catheter out through the incision. An endoscope is also used to remove the catheter.

U.S. Pat. No. 4,863,438, the disclosure of which is expressly incorporated herein in its entirety, shows a catheter that may be inserted into an established stoma from outside the body. A hollow mushroom-shaped resilient head on the tube may be distended by the insertion of a rigid obturator into the tube, with the distended head acting as a dilator to facilitate passing of the catheter through the stoma. Once the head clears the stoma, the obturator is withdrawn, and the head expands. A similar process is employed to remove this device, or mechanical traction may be used to remove the device.

In the gastronomy devices known in the art, the internal bolster generally has a planar wall which engages the patient's internal surface. In order to provide the desired resistance to withdrawal forces, the internal bolster is generally not compliant or pliable and, due to the arcuate shape of internal body tissues, typically has only point or line contact with the underlying tissue surface (i.e., stomach wall). As such, any withdrawal forces are concentrated on a limited portion of the subjacent tissue, and irritation and potential tissue deterioration and necrosis is a constant concern. Moreover, too much force or pressure on a limited area of tissue may damage the tissue, and may result in leakage around the gastrostomy device, ulceration, improperly fitting gastrostomy devices, and, ultimately, failure of the stoma.

Therefore, there exists a need in the art for an improved internal bolster for gastrostomy devices. Moreover, there exists a need in the art for a gastrostomy device internal bolster which is compliant and which interfaces in a more comfortable and anatomically correct fashion with the patient tissue internal surface. Finally, there is a need in the art for a gastrostomy device that is easily and quickly installed and that has an internal bolster which provides satisfactory resistance to withdrawal forces to prevent unintended removal of the bolster via the patient's stomach.

SUMMARY OF THE INVENTION

The present invention is directed toward a gastrostomy device which is easy to install within a patient and which includes an improved internal bolster. The present invention is also directed toward a gastrostomy device internal bolster which is compliant and which interfaces in a more comfortable manner with the patient. The present invention is further directed toward a gastrostomy device which is easy to install and which provides sufficient resistance to withdrawal forces.

In accordance with the present invention a gastrostomy device includes a tubular portion having an inner end and an outer end. An internal bolster extends radially from the tubular portion inner end. The internal bolster can be presented in either an installation configuration or a deployed configuration. In the installation configuration the internal bolster is elastically deformed or bent to be generally in-line with an axis of the tubular portion. Presentation of the internal bolster in the deployed configuration permits insertion of the gastrostomy device, i.e., internal bolster and tubular portion, through a patient's existing stoma. In the deployed configuration the bolster extends radially from the inner end of the tubular portion and generally transverse to the tubular portion axis.

In further accordance with the present invention, in the installation configuration a rod member extends generally parallel to the tubular portion. A projecting end of the rod member extends past the inner end of the tubular portion and is received within a pocket defined by the internal bolster. The internal bolster has a first part and a second part, the second part including the pocket. The first and second parts are preferably on relatively opposite sides of the tubular portion.

In further accordance with the present invention, a suture member extends through the rod member and includes a first portion and a second portion. The first portion projects from an outer end of the rod member. The second portion from the rod member projecting end and is operable to bind the first part of the internal bolster to the tubular portion.

In further accordance with the present invention, the internal bolster radially surrounds the tubular portion and has an inner surface and an outer surface. The inner surface faces the tubular portion, while the outer surface is directed away from the tubular portion. The outer surface includes the pocket. The inner surface is curved or arcuate such that the inner surface is relatively convex. The outer surface has a relatively planar portion surrounding the opening of the tubular portion and an arcuate portion surrounding the planar portion. As such, the internal bolster has a varying thickness which advantageously results in a variable flexibility.

In further accordance with the present invention, the internal bolster is relatively compliant or pliable to ease installation of the gastrostomy device and to reduce irritation following installation, while being sufficiently rigid to provide the necessary resistance to withdrawal forces. The internal bolster is formed from a material having a thickness, flexibility and shape to permit substantially full contact between the patient's tissue and the convex inner surface of the bolster.

In addition to the aforementioned device, the present invention is also directed toward a method for assembly and installation of the device.

BRIEF DESCRIPTION OF THE DRAWINGS

These and further features of the present invention will be apparent with reference to the following description and drawings, wherein:

FIG. 1a is a perspective view of a prior art dome-PEG device;

FIG. 1b is a side elevational view of the prior art dome-PEG device shown in FIG. 1a;

FIG. 2 is a perspective view of a gastrostomy device according to the present invention;

FIG. 3 is an enlarged perspective view of an internal bolster of the gastrostomy device shown in FIG. 2, shown in an installation configuration;

FIG. 4 is a perspective view of the internal bolster of FIG. 3, shown in a deployed configuration;

FIG. 5 is a top plan view of the internal bolster shown in FIG. 4;

FIG. 9b is an enlarged view of a portion of the cross-section of the internal bolster shown in FIG. 9a;

FIGS. 11–13 diagrammatically illustrate the sequential steps of installation of the gastrostomy device according to the present invention.

DETAILED DESCRIPTION OF THE PREFERRED EMBODIMENTS

Figure 7:
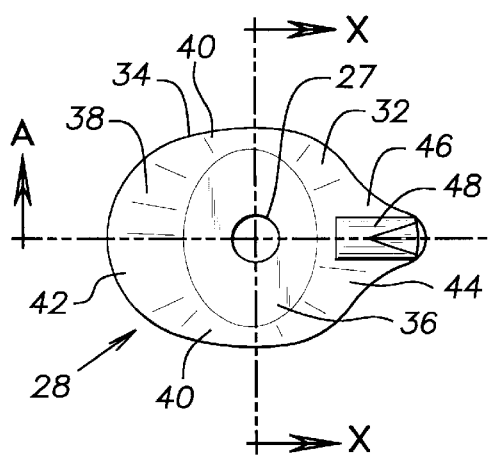
FIG. 7 is a left end elevational view of the internal bolster shown in FIGS. 4–6.
Figure 6:
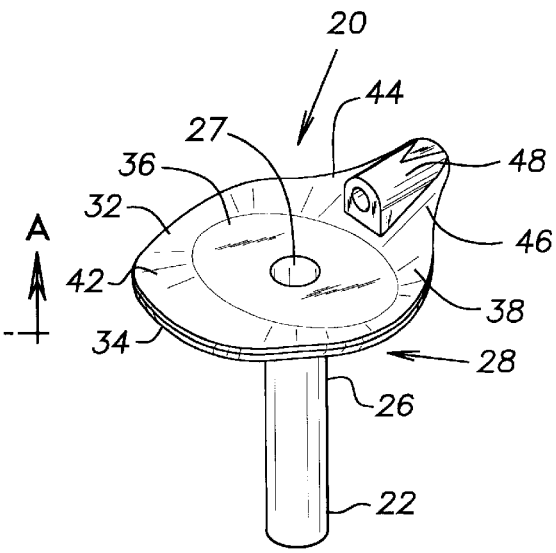
FIG. 6 is a front side elevational view of the internal bolster shown in FIGS. 4–5.
Figure 8:
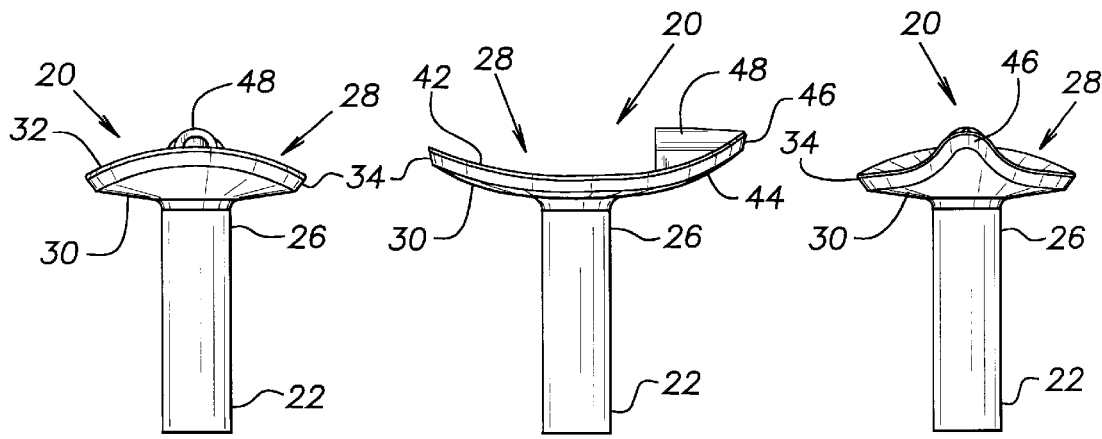
FIG. 8 is a left end elevational view of the internal bolster shown in FIGS. 4–7.
Figure 9A:
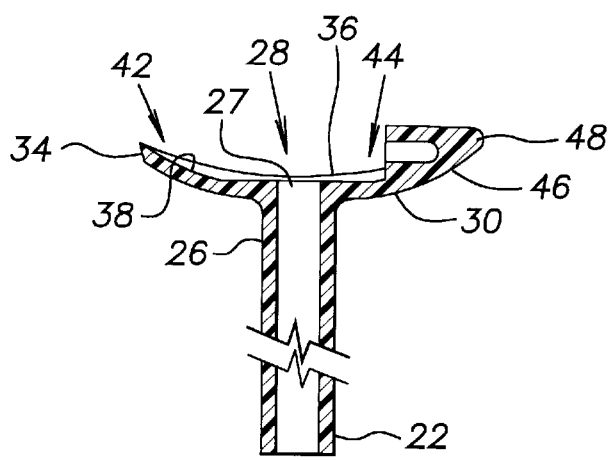
FIG. 9a is a cross sectional view of the internal bolster as seen along the center line A—A of FIG. 5.
Figure 9B:
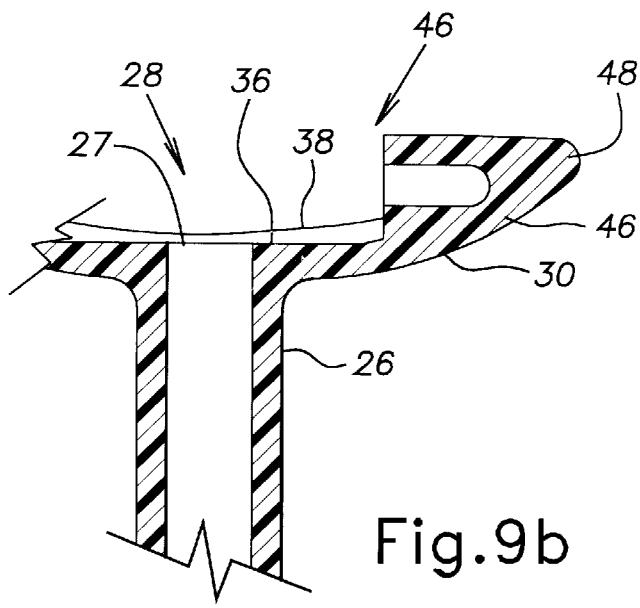
Figure 10:
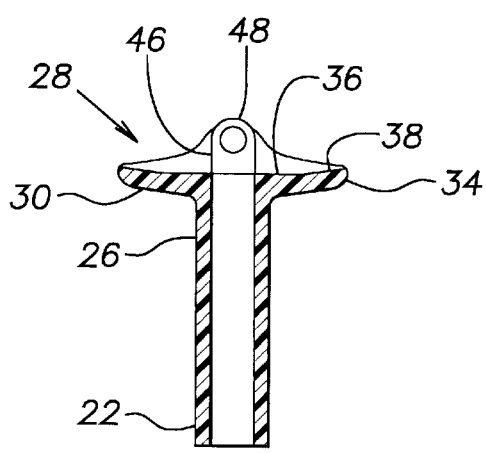
FIG. 10 is a cross sectional view of the internal bolster as seen along the line X—X of FIG. 5.

With reference to the drawing figures, a gastrostomy device 20 and method of installation according to the present invention is illustrated. The gastrostomy device 20 includes a tubular portion 22 having an outer end 24 and an inner end 26. The inner end 26 has an internal bolster 28 extending integrally and radially therefrom. The bolster normally extends generally transverse to a length direction of the tubular portion 22 (FIGS. 4–8) but, as will be apparent from the following description, is adapted to be reoriented to an installation configuration (FIGS. 2–3) which facilitates insertion of the gastrostomy device via a patient's stoma (FIGS. 9–11).

With reference to FIGS. 4–8, the internal bolster 28 is generally symmetrical about a center line A—A, and defines an inner surface 30 and an outer surface 32. The inner surface 30 faces the tubular portion 22 and is curved to a slightly convex shape. The curvature or radius of the inner surface 30 is generally constant as one moves outwardly from the tubular portion 22 toward a peripheral edge 34 of the internal bolster 28, as illustrated.

The outer surface 32 faces away from the tubular portion 22 and includes an inner oval-shaped portion 36 and a surrounding portion 38. The inner oval portion 36 is oriented generally transverse to the center line A—A, as illustrated. The outer surface 32 at the inner oval portion 36 is generally planar, while the surrounding portion 38 is slightly curved and generally matches the curvature of the inner surface 30. Accordingly, the outer surface 32 provides a generally flat-bottomed, concave or bowl-like shape. Due to the differing shapes of the inner and outer surfaces 30,32, the internal bolster 28 has a varying thickness, with the radially inner portion, which coincides with the inner oval portion 36, being relatively thicker than the remaining portion of the internal bolster 28.

Accordingly, the area immediately surrounding the tubular portion 22 is relatively less flexible than the remaining portion of the internal bolster 28, which aides in reconfiguring the internal bolster between the deployed and installation configurations, and provides desirable resistance to withdrawal forces. Moreover, the relatively increased resistance to flexing provided by the increased thickness at the inner oval portion 36 is directed transverse to the center line or length of the internal bolster 28 and tends to resist flexing or folding of lateral regions 40 of the internal bolster 28 toward the center line A—A thereof.

The internal bolster 28 has a first part 42 and a second part 44, each of which are bisected by the center line A—A. The first and second parts 42, 44 cooperate to provide the aforementioned lateral regions 40. The lateral regions 40 are secured in a deformed condition when the internal bolster 28 is in an installation configuration, as will be discussed more fully hereinafter.

The first part 42 of the internal bolster 28 is generally semi-oval. The second part 44 of the bolster 28 is integrally connected to the first part 42 and defines a tab-like member 46. The tab-like member 46 includes, on its outer surface, a pocket 48 for receipt of a rod member 50 to permit deformation of the internal bolster 28 from a deployed configuration (FIGS. 4–8) to an installation configuration (FIGS. 2–3), as will be discussed more fully hereinafter.

With specific reference to FIGS. 2–3, the rod member 50 preferably extends alongside and generally parallel to the tubular portion 22 and includes a projecting end 52 that extends beyond the opening 27 at the tubular portion inner end 26. The rod member projecting end 52 is removably inserted into the pocket 48 provided by the second part 44 of the internal bolster 28. As such, the second part 44 of the internal bolster is bent or deformed by the rod member 50 to be generally in-line with an axis of the tubular portion 22, as illustrated.

The rod member 50 is preferably hollow to accommodate a suture member or thread 56 that extends therethrough. A first hole or opening 58 is formed in an outer end 54 of the rod member a second opening 60 is formed in the projecting end 52 adjacent the pocket 48. The first and second openings 58, 60 communicate with the hollow interior of the rod member 50 and define a passageway through which the suture member 56 extends. Alternatively, the first opening may be formed in a circular end cap on the outer end of the rod member 50, such opening being co-axial with the rod member axis. In this alternative, the end cap opening is in communication with the hollow interior of the rod member and the suture member extends therethrough.

The suture member 56 cooperates with the rod member 50 to provide a secure yet easily removable restraint for the internal bolster 28 and thereby permits facile installation of the gastrostomy device within the body of the patient, as will be discussed more fully hereinafter with particular reference to FIGS. 9–11. To that end, a first portion 62 of the suture member 56 projects from the rod member outer end 54 and a second portion 64 of the suture member 56 projects from the rod member projecting end 52. More specifically, the suture member 56 extends through the rod member 50 and the first portion 62 projects from the first opening 58 while the second portion 64 projects from the second opening 60, as illustrated.

The second portion 64 of the suture member is configured as a suture wrap 66 that is wound around the first part 42 of the internal bolster 28 and the inner end 26 of the tubular portion 22 in a multiple slip-knot type configuration. As should be apparent from the drawings, the lateral regions 40 of the internal bolster 28 are folded, generally about the center line A—A, and about the rod member 50 and are retained in the folded position by the suture wrap 66. The first portion 62 of the suture member 56 may include a pull tab (not shown) to facilitate grasping and pulling thereof.

Pulling the first portion 62 of the suture member 56 relatively away from the suture wrap 66 causes the suture wrap to unravel. The suture wrap 66 releasably binds or holds the first part 42 of the internal bolster 28 against the tubular portion 22. The second part 44 of the internal bolster 28 is held away from the tubular portion 22 by the rod member 50. The suture wrap 66 and rod member 50 cooperate to stretch and deform the first and second parts 42, 44 of the internal bolster 28 from their normal or second configuration transverse to the axis of the tubular portion (FIGS. 4–8) to the installation configuration generally aligned with the axis of the tubular portion and the rod member (FIGS. 2–3).

The second portion 64 of the suture member 56 is wrapped around the first part 42 of the internal bolster 28 such that pulling the first portion 62 of the suture member 56 to move the suture member through the rod member 50 causes the suture wrap 66 to unravel and thereby release the first part 42 of the internal bolster from the tubular portion. Thereafter, the rod member 50 may be pulled or withdrawn to remove the rod member projecting end 52 from the pocket 48 and thereby permit the internal bolster 28 to move from the first position or installation configuration generally in line with the tubular portion 22 to the second position or deployed configuration generally transverse to the tubular portion 22.

Alternatively, it is contemplated that pulling the rod member 50 will both (either simultaneously or sequentially) withdraw the rod member projecting end 52 from the pocket 48 to release the second part 44 of the internal bolster 28 and pull the suture member 56 to cause the suture wrap 66 to unravel and release the first part 42 of the internal bolster. As such, in the contemplated alternative, only one operative step is required to release the first and second parts of the internal bolster and permit them to move from the first or installation configuration to the second or deployed configuration.

Naturally, it is considered apparent that the exact method or type of releasable suture wrap shown and described herein is exemplary in nature insofar as one skilled in the art will be able to use and develop numerous suture wrap patterns equivalent to the present without departing from the scope and spirit of the present invention. Therefore, the present invention covers and includes each of the numerous equivalent ways in which the internal bolster may be wrapped.

It is also considered apparent that the rod member 50 may extend through the tubular portion 22 instead of alongside same. However, having the rod member 50 external to the tubular portion 22 permits the tubular portion to be radially compressed by the suture wrap 66 and may, therefore, help minimize the profile of the gastrostomy device presented for insertion into the patient's stoma.

Figure 13:
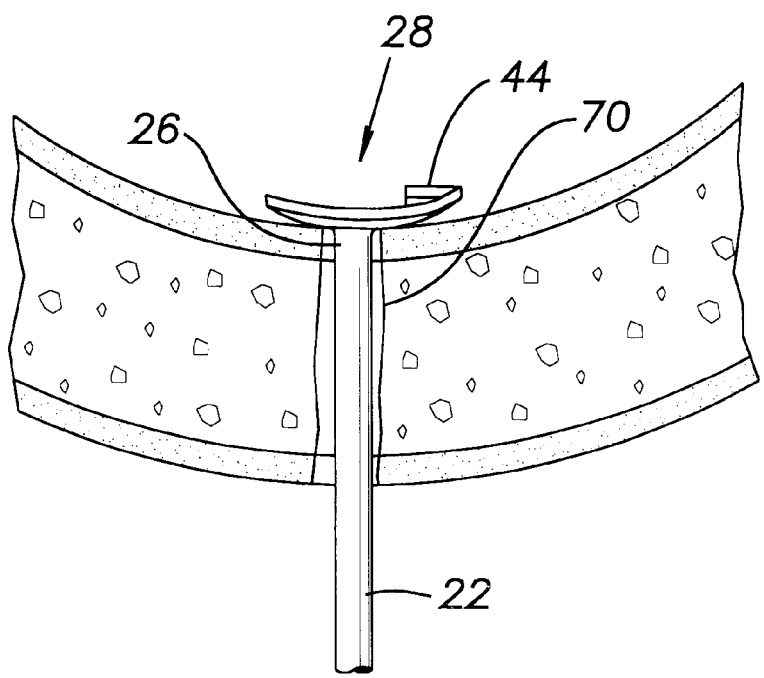

Turning to FIGS. 11–13, a method of installing the gastrostomy device 20 according to the present invention within a patient is illustrated. The gastrostomy device, with suture wrap 66 in place as described above, is aligned with and inserted through the patient's stoma 70. The suture wrap 66 and rod member 50 cooperate to maintain the internal bolster 28 in an undeployed or installation configuration to reduce the profile of the gastrostomy device 20 presented for insertion, and thereby permits insertion of the internal bolster 28 through the stoma 70. In this regard, compression of the tubular portion inner end 26 by the suture wrap 66 assists in reducing the profile of the gastrostomy device 20 presented for insertion. Once the inner portion of the gastrostomy device is within the interior of the patient, as shown in FIG. 10, the first portion 62 of the suture member 56 is pulled to cause the suture wrap 66 to unravel and release the internal bolster first part 42. Thereafter, the rod member 50 is pulled to withdraw the projecting end 52 from the pocket 48 and release the bolster second part 44. The bolster 28 and gastrostomy device 20 are thereafter in a deployed configuration.

Once the internal bolster 28 is in the deployed configuration, a clamp or exterior locking-type bolster may be attached to the tubular portion adjacent the patient's skin surface to prevent the gastrostomy device 20 from being pushed into the patient's body. The inclusion of scale indicia on the tubular portion permits eases measurement of tube migration.

The pull or withdrawal force required to remove a gastrostomy device 20 according to the present invention from a stoma has been tested and compared with similar pull forces required by dome-PEG devices (FIGS. 1a–1b). For conventional dome-PEG devices, the pull force required to deform and withdraw the internal bolster is generally around 8.4 pounds. However, for the gastrostomy device according to the present invention, the pull force is about 8.6 pounds. As such, the present invention provides a gastrostomy device having desirably high resistance to withdrawal forces (like conventional dome-PEG devices), while being easy to install (like stick-PEG devices). Naturally, the pull force of the gastrostomy device according to the present invention will vary in dependence upon a number of factors, such as the thickness and durometer of the materials used and, as such, the present invention is in no way limited to gastrostomy devices having any specific resistance to withdrawal forces.

While the preferred embodiments of the present invention are shown and described herein, it is understood that the present application will cover any and all modifications which fall within the scope of the claims appended hereto.

What is claimed is:

1. An internal bolster for a gastrostomy device with a tubular portion having an outer end and an inner end, the internal bolster comprising:
    an inner surface being generally convex in shape and being integrally attached to and radially surrounding the tubular portion inner end;
    an outer surface defining a pocket; and
    a first part being defined by a first portion of the outer surface and being defined by a first portion of the inner surface that is adjacent to the tubular portion inner end, the first part radially surrounding the tubular portion inner end; and
    a second part being defined by a second portion of the outer surface and being defined by a second portion of the inner surface, the second part at least partially surrounding the first part;
    wherein the internal bolster is resiliently movable between an installation configuration and a deployed configuration, and
    wherein the first part is less flexible than the second part.

2. An internal bolster according to claim 1, wherein the second part includes said pocket.

3. An internal bolster according to claim 2, wherein when the internal bolster is in the installation configuration the internal bolster is generally aligned with a longitudinal axis of the tubular portion.

4. An internal bolster according to claim 1, wherein the second part comprises a tab-like member, the tab-like member providing said pocket.

5. An internal bolster according to claim 1, wherein the first part is relatively thicker than the second part.

6. An internal bolster according to claim 1, wherein the internal bolster has a lengthwise center line and the first part is oriented generally transverse to the center line.

7. An internal bolster according to claim 1, wherein the first part is generally oval in shape.

8. An internal bolster for a gastrostomy device with a tubular portion having an outer end and an inner end, the internal bolster comprising:
    an inner surface facing toward the tubular portion, the inner surface being generally convex;
    an outer surface facing away from the tubular portion;
    an opening in communication with a passageway defined by the tubular portion;
    a first portion surrounding the opening having a first degree of flexibility;
    a second portion at least partially surrounding the first portion and having a second degree of flexibility;
    wherein the internal bolster is integrally attached to the tubular portion inner end and extends generally transverse to an axis of the tubular portion, wherein the internal bolster is resiliently movable between an installation configuration and a deployed configuration, and wherein the first portion is relatively less flexible than the second portion;
    wherein the outer surface includes a relatively planar portion surrounding the opening and an arcuate portion extending radially from the planar portion;
    wherein the relatively planar portion is generally oval in shape and is oriented generally transverse to a longitudinal center line of the internal bolster.

9. An internal bolster according to claim 8, wherein the first portion has a first thickness and the second portion has a second thickness, the first thickness being relatively greater than the second thickness.

10. An internal bolster according to claim 8, wherein the internal bolster includes a tab-like member that includes a pocket.

11. An internal bolster for a gastrostomy device with a tubular portion having an outer end and an inner end, the internal bolster comprising:
    an inner surface facing toward the tubular portion, the inner surface being generally convex;
    an outer surface facing away from the tubular portion;
    an opening in communication with a passageway defined by the tubular portion;
    a first portion surrounding the opening having a first degree of flexibility;
    a second portion at least partially surrounding the first portion and having a second degree of flexibility;
    wherein the internal bolster is integrally attached to the tubular portion inner end and extends generally transverse to an axis of the tubular portion, wherein the internal bolster is resiliently movable between an installation configuration and a deployed configuration, and wherein the first portion is relatively less flexible than the second portion;
    wherein the internal bolster is generally elongated in a lengthwise direction and symmetrical about a longitudinal center line, the bolster being asymmetrical about a center line oriented perpendicular to the longitudinal center line;

wherein the first portion has a first thickness and the second portion has a second thickness, the first thickness being relatively greater than the second thickness;

wherein the outer surface includes a relatively planar portion surrounding the opening and an arcuate portion extending radially from the relatively planar portion, the relatively planar portion corresponding to the first portion and the arcuate portion corresponding to the second portion;

wherein the relatively planar portion is generally oval in shape and is oriented generally transverse to the longitudinal center line.

* * * * *

UNITED STATES PATENT AND TRADEMARK OFFICE
CERTIFICATE OF CORRECTION

PATENT NO.    : 6,364,858 B1
DATED         : April 2, 2002
INVENTOR(S)   : George J. Picha It is certified that error appears in the above-identified patent and that said Letters Patent is hereby corrected as shown below:

Title page,
Item [56], References Cited, please add the following references:
-- 4,666,433    5/1987    Parks
5,549,657    8/1996    Stern et al. --

Signed and Sealed this

First Day of October, 2002

*Attest:*

JAMES E. ROGAN
*Director of the United States Patent and Trademark Office*

*Attesting Officer*